United States Patent [19]
Zebelein et al.

[11] Patent Number: 6,084,409
[45] Date of Patent: Jul. 4, 2000

[54] MAGNETIC RESONANCE SCANNER HAVING A UNITARY RADIO-FREQUENCY ARRANGEMENT

[75] Inventors: Guenther Zebelein, Moehrendorf; Ludwig Eberler, Postbauer-Heng; Bernd Stoeckel, Erlangen, all of Germany

[73] Assignee: Siemens Aktiengesellschaft, Munich, Germany

[21] Appl. No.: 08/888,838

[22] Filed: Jul. 7, 1997

[30] Foreign Application Priority Data

Jul. 5, 1996 [DE] Germany ............................ 196 27 210
May 27, 1997 [DE] Germany ............................ 197 22 193

[51] Int. Cl.$^7$ ........................................................ G01V 3/00
[52] U.S. Cl. .................. 324/318; 324/318; 324/307; 324/309; 324/322; 324/301; 600/410; 600/422
[58] Field of Search ..................................... 324/318, 307, 324/309, 322, 301; 600/410–422

[56] References Cited

U.S. PATENT DOCUMENTS

| | | | |
|---|---|---|---|
| 5,085,219 | 2/1992 | Ortendhal et al. | 324/318 |
| 5,197,474 | 3/1993 | Englund et al. | 324/318 |
| 5,311,134 | 5/1994 | Yamagata et al. | 324/318 |

*Primary Examiner*—John Barlow
*Assistant Examiner*—Brij B. Shrivastav
*Attorney, Agent, or Firm*—Hill & Simpson

[57] ABSTRACT

Magnetic resonance scanner has a radio-frequency system with transmission/reception antennas, and possibly a radio-frequency shield as well, and guides for a movable patient bed arranged in a basic field system and in a gradient system, with the electrical components of the radio-frequency system being embedded in a cylindrical, rigid carrier tube that penetrates the basic field system and the gradient system in the axial direction and which simultaneously serves as a carrier for the guides for the patient bed. The carrier tube is introducible as structural unit into the basic field and gradient system.

15 Claims, 3 Drawing Sheets

MAGNETIC RESONANCE SCANNER HAVING A UNITARY RADIO-FREQUENCY ARRANGEMENT

BACKGROUND OF THE INVENTION

1. Field of the Invention

The present invention is directed to a magnetic resonance imaging scanner of the type having a radio-frequency system with transmission/reception antennas that is arranged in a basic field system and in a gradient field system, as well as possibly having a radio-frequency shield, and having guides for a movable patient bed.

2. Description of the Prior Art

As basic components, a magnetic resonance scanner has three assemblies: basic field system, gradient field system and radio-frequency system (RF system). The basic field system serves the purpose of providing a strong, static magnetic field (typically 0.1–4 Tesla). The gradient system supplies a magnetic field adjustable in the low-frequency range to about 1 kHz with a linearly rising or decreasing curve in one or more directions (typically up to 30 mT/m). The RF system provides a magnetic field oscillating in the radio-frequency range at the nuclear magnetic resonance frequency of 42.45 MHZ/T essentially predetermined by the static magnetic field for exciting the nuclear spins and also serving for reception of the signals of the relaxing nuclear spins.

These three assemblies surround the patient to be examined in most magnetic resonance scanners in the sequence: RF system, gradient system and basic field system. The patient must be borne on a bed that can be moved into and out of the cylindrical opening.

A problem in all magnetic resonance scanners that has not been satisfactorily solved is the high noise level generated by the gradient system in the strong basic magnetic field because of the strong Lorentz forces. Additionally, the standard structure wherein the individual components of the RF system are built as segments into a tube containing the gradient coils is complicated in terms of assembly as well as being susceptible to malfunction. The structure of the bore for moving the patient bed into and out of the tube given this type of integration is optically disturbing for the patient and can only be kept sterile by means of extremely complicated measures. Finally, this structure also requires complicated internal cables for components of the RF system that are susceptible to malfunction. A structure that is relatively radially thick overall is thus necessary, as a result of which the free diameter of the basic field system must be enlarged in order to provide a predetermined clear (unobstructed) inside diameter for moving the patient bed. This free diameter (warm bore) of the basic field system, however, largely determines the price of the basic field magnet.

These difficulties also apply to a magnetic resonance scanner of the type disclosed in U.S. Pat. No. 5,197,474. Here, the radio-frequency coil is rigidly connected to the portion of a two-part bed and is inserted in common therewith into the basic field system and the gradient system. The cabling must thereby also be drawn in, which likewise enlarges the free diameter of the basic field system.

In U.S. Pat. No. 4,654,596, the radio-frequency coil is wound onto a carrier sleeve whose length corresponds to the length of the radio-frequency coil winding. This short tube section lies inside the scanner and again impedes the introduction and withdrawal of the patient, particularly because the leads here must again be loosely arranged in the through opening for the patient.

U.S. Pat. No. 4,634,980 discloses a magnetic resonance scanner for head examinations wherein the radio-frequency coil, independently of the patient bed which is introducible into the basic field and gradient system, is displaceable over a tongue-shaped extension of the patient bed that accepts the patient's head. This fashioning cannot be transferred at all to a scanner for whole-body examinations because it would then not be possible at all to move the radio-frequency coil over the patient bed which is movable in the basic field and gradient system.

SUMMARY OF THE INVENTION

An object of the present invention is to provide a magnetic resonance scanner of the type initially described which has a simple structure not prone to malfunction as well as an optically pleasing and easily disinfected, smooth inside bore for the patient bed, and which provides soundproofing for the high noise level of the gradient system but still enables easy replacement for any repairs which may become necessary.

This object is achieved in a scanner according to the invention wherein the electrical components of the RF system are inserted into a cylindrical, axially stiff supporting tube that penetrates the basic field system and the gradient system in the axial direction and that simultaneously serves as carrier for the guides for the patient bed, and which is introducible as a structural unit into the basic field and gradient system, with the carrier tube preferably penetrating the gradient system in noncontacting fashion.

As a result of this fashioning of the RF system, a complicated mounting of separate radio-frequency segments at the inside wall of the gradient coil carrier tube is eliminated. In this way, a closed, smooth tube structure is obtained that, due to the smooth inside surface, keeps the claustrophobic discomfort of the patient low, which advantage can be further promoted in an embodiment of the invention wherein support shells that are open at both ends are applied to the carrying tube. The carrying tube is thus fashioned as a closed tube only in the middle section that is arranged in the magnet system, whereas the system length is kept so short by the upwardly open support shells, which can serve as a free suspension in the basic field system, or possibly outside this basic field system as well. This also results in claustrophobic discomfort of the patient being kept as low as possible for the patient passing therethrough.

Various self-supporting designs can be provided in order to be able to realize the cantilevered support of the inventive carrying tube containing the RF system in the surrounding magnet system without significant sag and thus without varying the predetermined air gap. Either the carrier tube can be constructed of, preferably, fiber-reinforced plastic layers and high-resistance foam layers in alternation, or the carrier tube can be formed by hollow honeycomb ring layers of plastic with a radially proceeding longitudinal honeycomb axis that are separated by plastic foils (prepreg layers). As a result of this honeycomb structure, which is generally known, for example, from aircraft construction, an extremely stiff, stable and extremely lightweight structure is achieved that is suited for embedding the radio-frequency components as well as assuming the patient support. Moreover, this design enables an especially simple fabrication wherein the carrier tube is constructed of plies glued to one another that are layered on top of one another on a winding spindle, with the antenna and/or an RF shield being embedded as foils into the carrier tube laminate. Additionally, this supporting structure has the advantage that only slight RF losses occur and since $\epsilon_r \approx 1$ applies, the resonant frequency is also hardly influenced.

A very easy replacement of the RF system as a simple structural unit insertable into the magnet system is possible as a result of the inventive structure. Moreover, the closed structure of the carrier tube offers excellent fire protection, protection against accidental contact with high-voltage, simple disinfection and good noise protection due to the honeycomb system that can even be improved by filling the openings of the honeycombs are filled with insulating material. Because no additional bearing system, for example for the guidance of the patient bed, is needed, a considerable space-saving and thus a smaller diameter of the "warm bore" is achieved, resulting in a considerable cost saving since it is thus possible to make the basic field system smaller. By contrast to known scanners with segments for the RF system installed in the carrier tube of the gradient system and hard-wired therein, the risk of tearing off electrical contacts is minimized in the inventive, closed system. Additionally, no undefinable contact locations of metal to metal or plastic to plastic exist and, finally, foreign objects such a dust, solder splatters, nuts, screws or the like can be precluded as possible causes of malfunctions. Lastly, the carrier tube for the RF system constructed with a honeycomb structure and the support for the patient bed also has the advantage of exhibiting a fixed resonant frequency without the risk of microphone effects.

DESCRIPTION OF THE PREFERRED EMBODIMENTS

Figure 1:
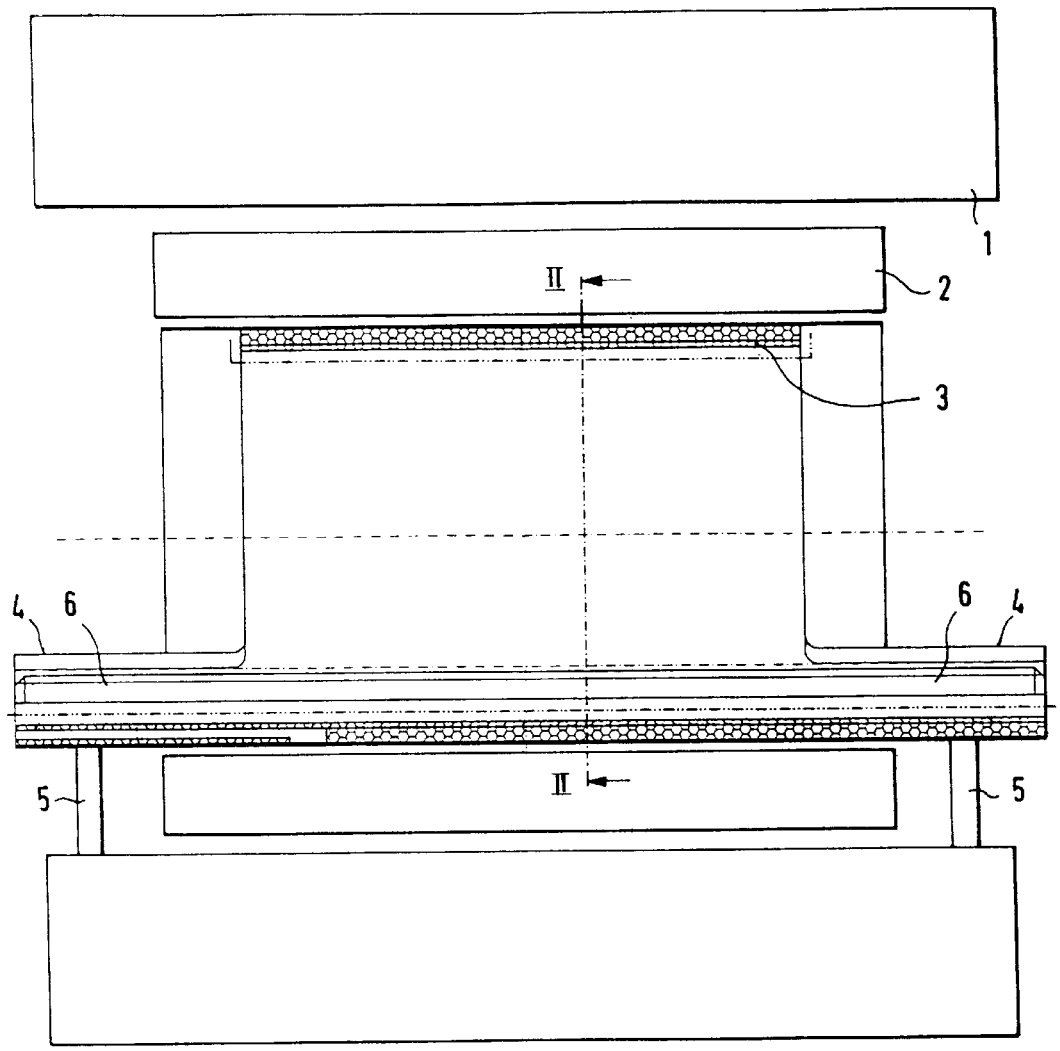
FIG. 1 is a schematic section through a magnetic resonance scanner with an inventive RF carrier tube.
Figure 2:
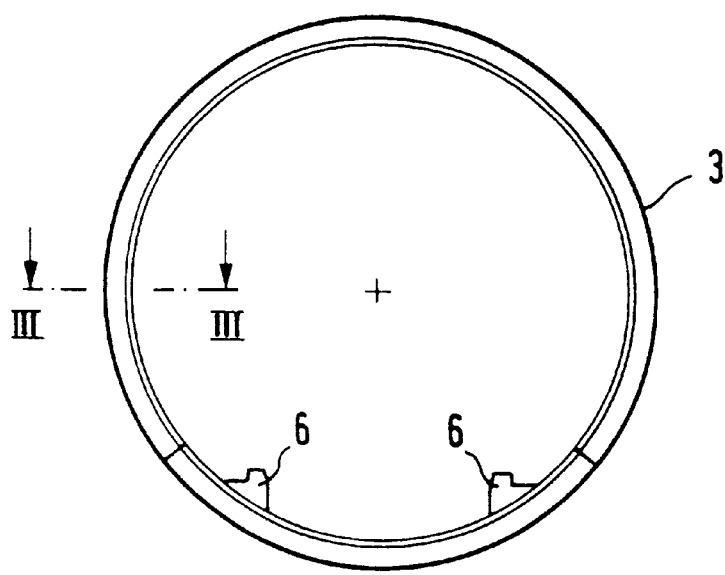
FIG. 2 is a section along the line II—II in FIG. 1.

FIG. 1 schematically shows the magnet 1 of the basic field system as well as the tubular structure of the gradient system 2 arranged in this basic field system. Inventively, the RF system can be seen in the inside of the gradient system in the form of a carrier tube 3 containing the corresponding electrical components and constructed as a honeycomb structure. The carrier tube 3 is fashioned as a closed tube only in the central section within the magnet system, whereas both ends thereof are provided with upwardly open support shells that are seated in the basic field magnet 1 via supports 5 that are only schematically indicated. The entire RF carrier tube is thus arranged cantilevered in the magnet system and, accordingly, can be inserted and in turn withdrawn for assembly purposes in a simple way. As can be seen particularly from FIG. 2, guide rails 6 for the displacement of a patient bed (not shown) are molded in or glued on in the design of the carrier tube 3 provided with closed outside surfaces, so that a separate, often self-supporting arrangement of these guide rails in the magnet system as was hitherto standard is completely superfluous. The connection of the guide rails 6 for the patient bed to the RF carrier tube 3 is completely mechanically decoupled from the magnet system, however, thereby producing the advantage of avoiding a direct structure-borne transmission of sound from the gradient system onto these guides rails 6. The noise load on the patient is thereby substantially reduced from the very outset.

Additionally, this noise load is damped because the RF carrier tube 3 itself produces an excellent sound damping due to its internal honeycomb structure, which also is not stressed by any of direct contact with the gradient system. The free suspension in the basic field magnet offers a very effective decoupling from the noise level generated in the gradient system.

Figure 3:
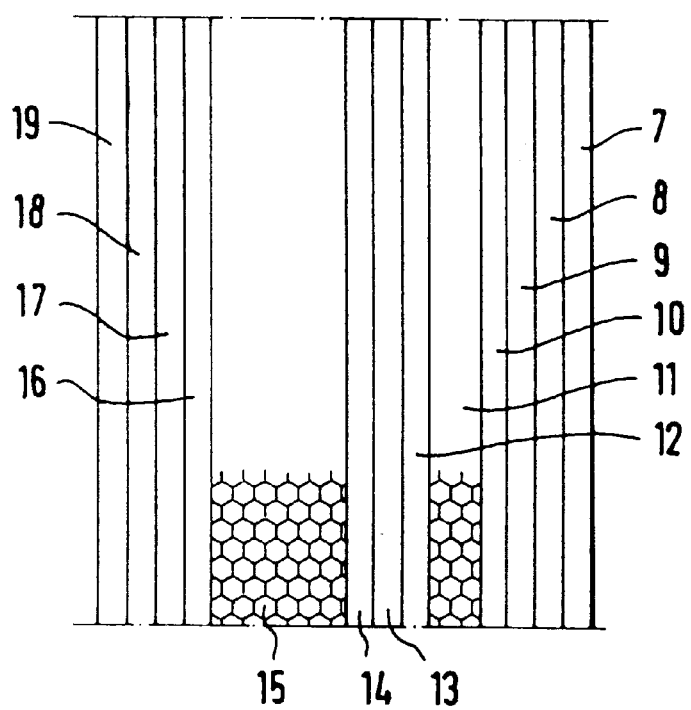
FIG. 3 is a highly enlarged section through the wall of the inventive RF carrier tube roughly along the line III—III in FIG. 2.

FIG. 3 schematically shows a number of closed plastic foils 7 through 10, referred to as prepreg layers, that are layered on top of one another on a winding spindle. The individual layers can be fashioned on the order of magnitude of 0.2 through 0.5 mm thick and can be of different materials as well. A first hollow honeycomb ply 11 is wound onto this inside ply; the honeycomb structure indicated in FIG. 3 only serves for identifying this layer as a hollow honeycomb layer. Of course, the honeycombs do not proceed in the circumferential direction, as shown, but proceed radially with respect to the tube structure. These layers include a foil adhesive layer 12, a radio-frequency antenna 13 fashioned, for example, as a punched foil, and another foil adhesive layer 14. The ply 15 is a honeycomb layer which is followed, finally, by three more prepreg layers 16, 17 and 18. Finally, a radio-frequency shield 19 is provided. The shield 19 could alternatively be formed as one of the intermediate plies of the inventive hollow honeycomb layer structure of the carrier tube laminate.

Openings (not indicated in the drawing for clarity) accessible from the outside of the inventive carrier tube are provided as access for contacting the antenna and, as warranted, further radio-frequency component parts that could be embedded into the honeycomb structure.

Figure 4:
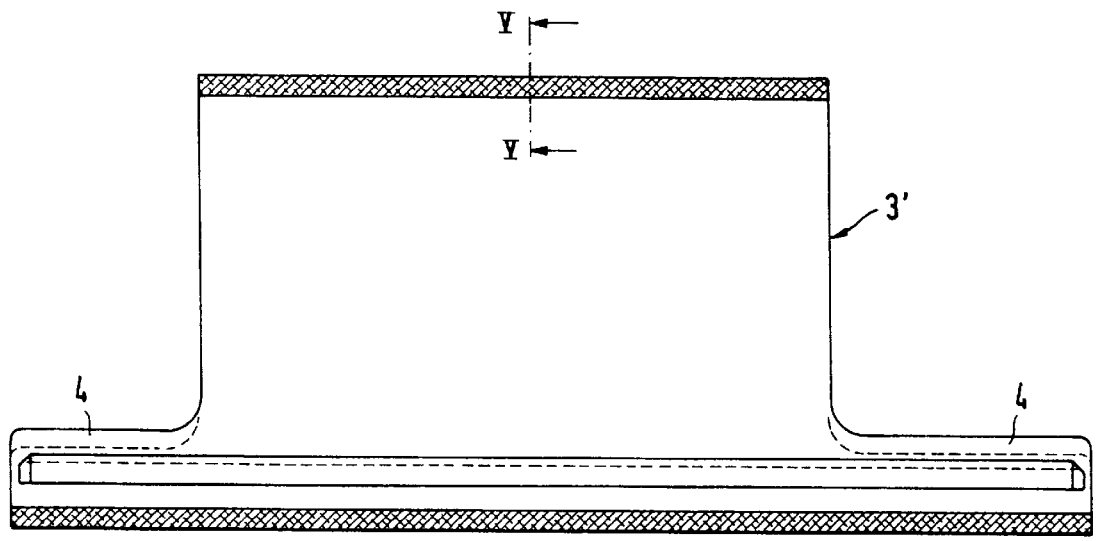
FIG. 4 is a longitudinal section through an inventive RF carrier tube in high-resistance foam structure.
Figure 5:
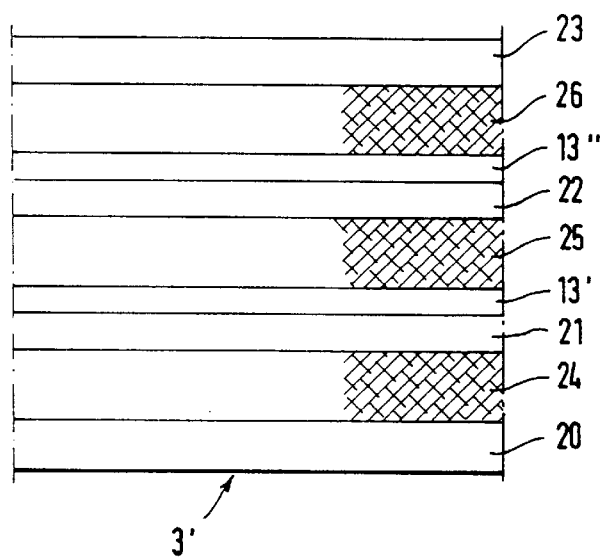
FIG. 5 is a section along the line V—V in FIG. 4.

FIGS. 4 and 5 show a carrier tube 3' modified compared to FIGS. 1 and 3. As FIG. 5 shows, this carrier tube 3' has a different ply structure. In addition to a number of fiberglass-reinforced plastic layers 20 through 23 as well as three high-resistance foam layers 24, 25 and 26, the radio-frequency antenna, divided in two, is accommodated in the layers 13' and 13".

Although modifications and changes may be suggested by those skilled in the art, it is the intention of the inventors to embody within the patent warranted hereon all changes and modifications as reasonably and properly come within the scope of their contribution to the art.

We claim as our invention:

1. A radio-frequency arrangement for use in a magnetic resonance scanner having a gradient system and a basic field system, comprising:

a cylindrical, rigid carrier tube insertable during assembly into said basic field system and said gradient system in an axial direction;

a radio-frequency system having at least one transmission/reception antenna, said transmission/reception antenna being embedded in said carrier tube;

guides disposed in an interior of said carrier tube adapted for receiving and guiding a patient bed;

said carrier tube, said transmission/reception antenna embedded therein and said guides comprising a unitary structural unit; and a mount for rigidly attaching said unitary structural unit to said basic field system and allowing detaching of said unitary structural unit for removal of said unitary structural unit from said basic field system.

2. A radio-frequency arrangement as claimed in claim 1 wherein said mount supports said carrier tube out of contact with said gradient system.

3. A radio-frequency arrangement as claimed in claim 1 wherein said carrier tube comprises upwardly open support shells respectively disposed at opposite ends of said carrier tube forming a part of said mount.

4. A radio-frequency arrangement as claimed in claim 1 wherein said carrier tube comprises a plurality of alternating fiberglass-reinforced plastic layers and high-resistance foam layers.

5. A radio-frequency arrangement as claimed in claim 1 wherein said carrier tube comprises a laminate formed by a plurality of closed plastic foils and at least one annular honeycomb layer, said honeycomb layer having a plurality of honeycomb openings therein, each opening having a longitudinal axis and the longitudinal axes of said opening proceeding radially from said axial direction.

6. A radio-frequency arrangement as claimed in claim 5 wherein said at least one annular honeycomb layer is comprised of plastic.

7. A radio-frequency arrangement as claimed in claim 5 wherein said plastic foils respectively comprise prepreg layers.

8. A radio-frequency arrangement as claimed in claim 5 wherein said laminate comprises a plurality of plies, formed by said plastic foils, glued to one another and layered on top of one another on a winding spindle.

9. A radio-frequency arrangement as claimed in claim 5 wherein said transmission/reception antenna comprises conductive foils embedded into said laminate.

10. A radio-frequency arrangement as claimed in claim 5 further comprising a radio-frequency shield comprising conductive foils embedded into said laminate.

11. A radio-frequency arrangement as claimed in claim 5 further comprising a radio-frequency shield, and wherein each of said radio-frequency shield and said transmission/reception antenna comprise conductive foils embedded into said laminate.

12. A radio-frequency arrangement as claimed in claim 5 further comprising insulating material filling said openings of said at least one annular honeycomb layer.

13. A radio-frequency arrangement as claimed in claim 1 wherein said carrier tube has a smooth exterior surface.

14. A radio-frequency arrangement as claimed in claim 1 wherein said basic field system includes a basic field magnet, and wherein said mount supports said carrier tube on said basic field magnet.

15. A radio-frequency arrangement as claimed in claim 1 further comprising a radio-frequency shield embedded in said carrier tube and comprising a component of said unitary structural unit.

* * * * *